United States Patent
Damm (10) Patent No.: US 12,245,932 B2
(45) Date of Patent: Mar. 11, 2025

(54) CARTRIDGE AND INJECTOR WITH THE CARTRIDGE

(71) Applicant: Carl Zeiss Meditec AG, Jena (DE)

(72) Inventor: Niklas Damm, Berlin (DE)

(73) Assignee: Carl Zeiss Meditec AG, Jena (DE)

( * ) Notice: Subject to any disclaimer, the term of this patent is extended or adjusted under 35 U.S.C. 154(b) by 251 days.

(21) Appl. No.: 17/838,249

(22) Filed: Jun. 12, 2022

(65) Prior Publication Data

US 2022/0296364 A1   Sep. 22, 2022

Related U.S. Application Data (63) Continuation of application No. PCT/EP2020/085601, filed on Dec. 10, 2020.

(30) Foreign Application Priority Data

Dec. 12, 2019   (DE) .................... 10 2019 134 183.3

(51) Int. Cl.
   *A61F 2/16* (2006.01)
   *A61M 5/31* (2006.01)

(52) U.S. Cl.
   CPC .......... *A61F 2/1678* (2013.01); *A61F 2/1691* (2013.01); *A61M 2005/3118* (2013.01)

(58) Field of Classification Search
   CPC .... A61F 2/1678; A61F 2/1691; A61F 2/1675; A61F 2/1662; A61F 2/167; A61M 2005/3118
   See application file for complete search history.

(56) References Cited

U.S. PATENT DOCUMENTS

| 2005/0065534 A1 | 3/2005 | Hohl |
| 2014/0012277 A1* | 1/2014 | Matthews ............... A61F 2/167 606/107 |
| 2022/0192818 A1* | 6/2022 | Raquet ................... A61F 2/167 |

FOREIGN PATENT DOCUMENTS

| DE | 102005004598 A1 | 8/2006 |
| EP | 937443 A2 | 8/1999 |

(Continued)

OTHER PUBLICATIONS

Written Opinion dated Jun. 28, 2021 of international application PCT/EP2020/085601 (on which this application is based), and English Language Translation thereof.

(Continued)

*Primary Examiner* — Sarah A Long
(74) *Attorney, Agent, or Firm* — Ewers IP Law PLLC; Falk Ewers (57) ABSTRACT

A cartridge includes a first opening, a second opening, a channel, an intraocular lens arranged in the channel, and a cartridge plunger arranged in the channel and configured to firstly preload the intraocular lens by moving the cartridge plunger towards the first opening, then to fold the lens by moving it in the tapered region, and finally to push the lens out of the channel via the first opening. The cartridge is configured to be coupled to a syringe such that a fluid can be injected into the channel, and as a result the cartridge plunger can be propelled in a movement direction towards the first opening. The cartridge plunger includes a first cartridge plunger longitudinal end, a second cartridge plunger longitudinal end, and a fluid line via which the fluid can be injected from the second to the first cartridge plunger longitudinal end and finally to the intraocular lens.

9 Claims, 10 Drawing Sheets

(56) References Cited

FOREIGN PATENT DOCUMENTS

GB          2585888 A  *  1/2021  ........... A61F 2/1451
WO         03045285 A1    6/2003

OTHER PUBLICATIONS

Office Action issued in German Patent Application No. DE 10 2019 134 183.3, dated Sep. 30, 2020 (from which this application claims priority) and English language translation thereof.
International Search Report dated Jun. 28, 2021 of international application PCT/EP2020/085601 on which this application is based.

* cited by examiner

CARTRIDGE AND INJECTOR WITH THE CARTRIDGE

CROSS REFERENCE TO RELATED APPLICATIONS

This application is a continuation application of international patent application PCT/EP2020/085601, filed Dec. 10, 2020, designating the United States and claiming priority to German application 10 2019 134 183.3, filed Dec. 12, 2019, and the entire content of both applications is incorporated herein by reference.

TECHNICAL FIELD

The disclosure relates to a cartridge and an injector with the cartridge.

BACKGROUND

In cataract treatment of an eye, an incision is conventionally made in the cornea of the eye, said incision being large enough to allow a cannula to be inserted through the incision into the eye. After the incision has been made in the cornea, the lens of the eye is broken up by phacoemulsification and then sucked out of the capsular bag of the eye. Thereafter, an intraocular lens is inserted into the capsular bag with an injector. For this purpose, the injector has a plunger which is set up to push the intraocular lens out of the injector through an injector tip. There are injectors in which the intraocular lens is only inserted into the injector shortly before the cataract treatment. This is performed for example by inserting a cartridge, in which the intraocular lens is located, into the injector. It is disadvantageous that the cartridge and the injector are components that have an expensive and complicated structure.

SUMMARY

It is an object of the disclosure to provide a simple structure for a cartridge and an injector with such a cartridge.

The cartridge according to an aspect of the disclosure has a first opening, a second opening, a channel, which extends from the first opening to the second opening and has a taper, an intraocular lens, which is arranged in the channel between the first opening and the second opening, and a cartridge plunger, which is arranged in the channel between the intraocular lens and the second opening and set up to first preload the intraocular lens by displacing the cartridge plunger toward the first opening, then to fold the intraocular lens by displacing it in the taper and then to push the lens out of the channel via the first opening, wherein the cartridge is set up to be coupled to a syringe, such that a fluid can be forced into the channel via the second opening with the syringe and the cartridge plunger can thereby be propelled in a direction of insertion toward the first opening, wherein the cartridge plunger has a first cartridge-plunger longitudinal end, a second cartridge-plunger longitudinal end and a fluid line, which extends from the first cartridge-plunger longitudinal end to the second cartridge-plunger longitudinal end and via which the fluid can be forced from the second cartridge-plunger longitudinal end to the first cartridge-plunger longitudinal end and then to the intraocular lens.

Coupling the cartridge to the syringe provides an injector with which the intraocular lens can be inserted into a capsular bag of an eye. Both the cartridge, which has the channel with the taper and the cartridge plunger, and the syringe are components with a simple structure. The injector can thus be produced simply and inexpensively. The provision of the fluid line makes it possible to wet the intraocular lens with the fluid before the intraocular lens is inserted into the capsular bag of the eye. As a result, friction of the intraocular lens in the channel can be reduced. By choosing the form of the fluid line, it is also possible to set how strongly the cartridge plunger is propelled by the fluid. If the fluid line has a small cross section, the cartridge plunger is propelled rather strongly, and a rather larger quantity of the fluid reaches the intraocular lens. If the fluid line has a large cross section, the cartridge plunger is propelled rather weakly, and a rather small amount of fluid reaches the intraocular lens.

It is typical that the first cartridge-plunger longitudinal end, projected in the direction of insertion, has a larger cross section than the second cartridge-plunger longitudinal end, projected in the direction of insertion. It is particularly typical that the cartridge plunger seals the channel in the area of the first cartridge-plunger longitudinal end, such that no fluid can pass through the cartridge plunger on its outer circumference. This achieves the effect that the intraocular lens, in particular a haptic element of the intraocular lens, cannot be clamped between the cartridge plunger and a wall of the channel. In addition, the fluid only reaches the intraocular lens via the fluid line.

The channel typically has a first channel portion, in which the second cartridge-plunger longitudinal end is arranged before the fluid is forced into the channel and which has a first cross section, the normal of which is arranged parallel to the direction of insertion and essentially corresponds to the second cartridge-plunger longitudinal end projected in the direction of insertion, and a second channel portion, which is arranged between the first channel portion and the first opening and has a second cross section, the normal of which is arranged parallel to the direction of insertion and which is larger than the first cross section, wherein the distance from the first opening to the first channel portion is longer than the extent of the cartridge plunger in the direction of insertion. This achieves the effect that, at the beginning of the displacement of the cartridge plunger toward the first opening, the fluid acts only on the second cartridge-plunger longitudinal end. If the cartridge plunger is displaced further toward the first opening, the second cartridge-plunger longitudinal end moves out of the first channel portion. This allows the fluid to pass the longitudinal end and to act on a larger area than at the beginning of the displacement. Assuming that the pressure of the fluid remains the same during the entire displacement, a higher force acts on the cartridge plunger after the second cartridge-plunger longitudinal end has left the first channel portion. Because the distance from the first opening to the first channel portion is longer than the extent of the cartridge plunger, this occurs while the cartridge plunger is still completely within the channel. As the force increases during the displacement of the cartridge plunger, this can advantageously compensate for the fact that the intraocular lens is squeezed further and further as it is displaced toward the first opening and thus generates an ever larger force of resistance.

It is typical that the cartridge plunger has a first portion, which has the first cartridge-plunger longitudinal end and is flexible, a second portion, which has the second cartridge-plunger longitudinal end, and a third portion which is arranged between the first portion and the second portion and has a recess, which is set up to receive parts of the first portion when the cartridge plunger enters the taper. As a result, the first portion can bend in the direction of the second cartridge-plunger longitudinal end when the cartridge plunger is displaced into the taper and can move into the recess in a space-saving manner. It is particularly typical that the first portion has a groove on its side facing away from the intraocular lens. As a result, the first portion can bend more easily in the direction of the second cartridge-plunger longitudinal end.

The fluid line typically has a curve. This increases the flow resistance in the fluid line, as a result of which less of the fluid reaches the intraocular lens and the cartridge plunger is propelled more strongly. For example, the curve may be part of a meandering portion or a helical portion of the fluid line.

The intraocular lens typically has an optical body which is arranged completely between the taper and the cartridge plunger. This places the optical body outside the taper and in a relaxed state before the cartridge is coupled to the syringe. Therefore, creep effects in the optical body can be avoided during storage of the intraocular lens. Since the cartridge is only coupled to the syringe shortly before a cataract treatment and only then can the optical body be brought into a preloaded state, no creep effects occur. The intraocular lens particularly typically has a haptic element, which is arranged in the channel in such a way that both the optical body and the haptic element are in a relaxed state. As a result, there are no creep effects in the haptic element either.

It is typical that the channel is straight. As a result, the channel has no deflections or curves and neither the cannula nor the cartridge plunger nor the intraocular lens have to be guided around a deflection or a curve.

The cartridge typically has a tip, in which the first opening is arranged, and which is set up to be inserted into the capsular bag of an eye.

It is typical that the cartridge has a cartridge adapter, which is set up to be in engagement with a syringe adapter of the syringe to couple the cartridge to the syringe. By providing the cartridge adapter, the cartridge can be coupled to the syringe particularly easily.

The cartridge adapter is typically a male adapter of a Luer connection or a female adapter of a Luer connection. Alternatively, the cartridge adapter is typically part of a clamping closure, a snap-in closure, a bayonet closure or a screw closure. If the cartridge adapter is part of a screw closure, the cartridge adapter has an external thread or an internal thread.

The injector according to an aspect of the disclosure has the cartridge and the syringe, wherein the cartridge is coupled to the syringe, the syringe has the fluid and the injector is set up to displace the cartridge plunger in the direction of insertion toward the first opening by forcing the fluid into the channel via the second opening with the syringe.

The syringe typically has a cannula through which the fluid can be forced out of the syringe. This allows the syringe to be used for other tasks before the cartridge is coupled to the syringe. For example, the fluid can be introduced into the canal with the syringe to lubricate the cartridge and/or the intraocular lens, or the fluid can be introduced into the capsular bag.

It is typical that the cannula is of such a length that when the cartridge is coupled to the syringe, the cannula displaces the cartridge plunger in the direction of the first opening sufficiently far to preload the intraocular lens. It is also conceivable that the intraocular lens is folded thereby. By preloading and optionally folding the intraocular lens, a sealing of the channel is brought about.

The cartridge plunger typically has at its end facing the syringe a cartridge plunger recess, which is set up to receive the longitudinal end of the cannula facing the cartridge plunger when the cartridge is coupled to the syringe. Due to the cartridge plunger recess, the cartridge plunger has a defined point at which the cannula makes contact with the cartridge plunger.

It is typical that the cartridge has a cartridge adapter, and the syringe has a syringe adapter through which the cannula extends, wherein the cartridge adapter and syringe adapter are in engagement with one another, whereby the cartridge is coupled to the syringe and the injector is sealed in the region of the cartridge adapter and the syringe adapter. As a result, it can advantageously be avoided that, when it is forced out of the syringe, the fluid escapes from the injector via the second opening.

The cartridge adapter and the syringe adapter are typically in positive engagement with one another. This makes it possible to determine with a high level of accuracy how far the cannula penetrates the canal when the cartridge is coupled to the syringe. This also makes it possible to determine with a high level of accuracy how far the cannula displaces the cartridge plunger in the direction of the first opening and how far the cartridge plunger pushes the intraocular lens into the taper as a result.

It is typical that the cartridge adapter and the syringe adapter form a Luer connection, a clamping closure, a snap-in closure, a bayonet closure or a screw closure. If the cartridge adapter is part of a screw closure, the cartridge adapter has an external thread or an internal thread.

The syringe typically has a cylinder and a syringe plunger, which is mounted in the cylinder so that it can be displaced longitudinally, wherein the cylinder and the syringe plunger delimit a cylinder interior, in which the fluid is arranged, and which is connected to the cannula in a fluid-conducting manner. As a result, the syringe has a particularly simple structure.

The fluid typically includes a lubricant and/or a physiological saline solution or consists of the lubricant and/or the physiological saline solution. The lubricant may be an ophthalmic viscoelastic device (OVD).

A method of assembling the injector includes the steps of: a) providing the cartridge; b) providing the syringe containing the fluid; c) coupling the cartridge to the syringe, such that the injector is produced and such that the fluid can be forced into the channel via the second opening with the syringe and the cartridge plunger can thereby be propelled in the direction of the first opening.

A method for operating the injector includes the steps of: a) providing the cartridge; b) providing the syringe containing the fluid; c) coupling the cartridge to the syringe, such that the injector is produced; d) pressing the syringe, as a result of which the fluid enters the channel via the second opening and reaches the intraocular lens via the fluid line and displaces the cartridge plunger in the direction of the first opening, whereby the cartridge plunger first preloads the intraocular lens, then folds the intraocular lens by displacing it in the taper and then pushes it out of the channel via the first opening.

BRIEF DESCRIPTION OF THE DRAWINGS

The disclosure will now be described with reference to the drawings wherein.

DESCRIPTION OF EXEMPLARY EMBODIMENTS

Figure 1:
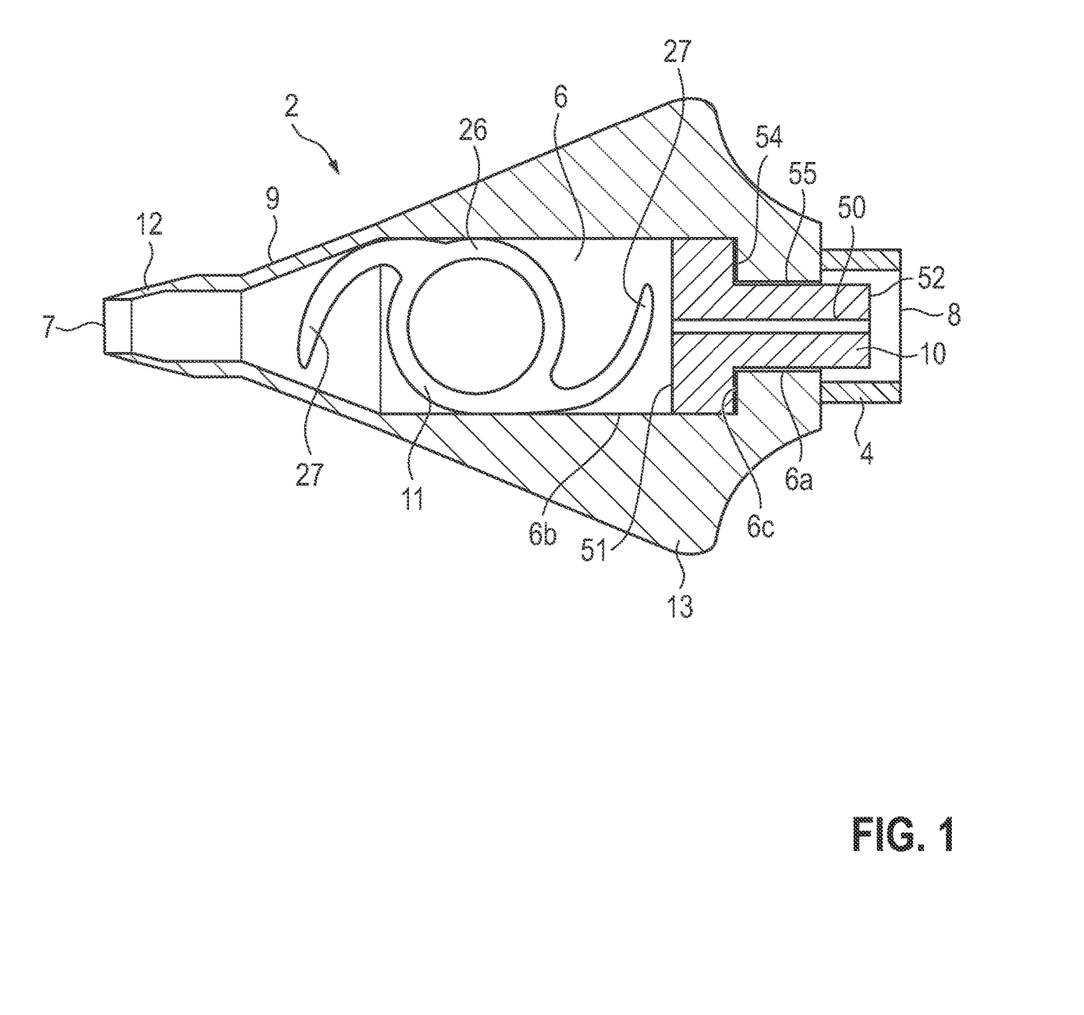
FIG. 1 shows a cartridge.
Figure 3:
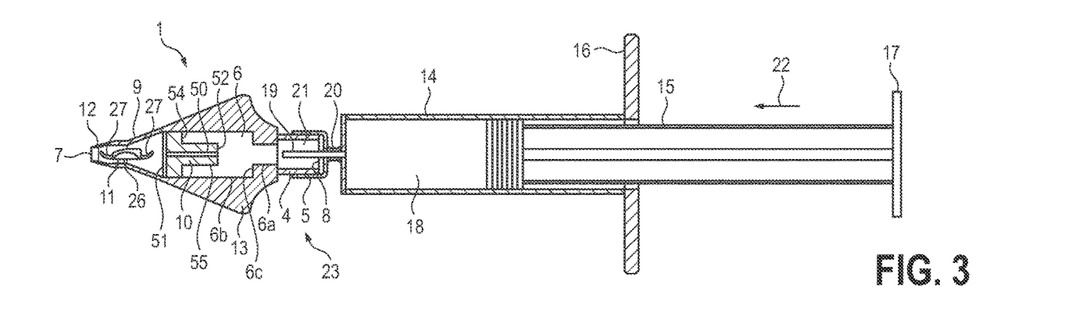
FIG. 3 shows an injector, wherein the cartridge is coupled to the syringe and the syringe plunger in a second position.
Figure 4:
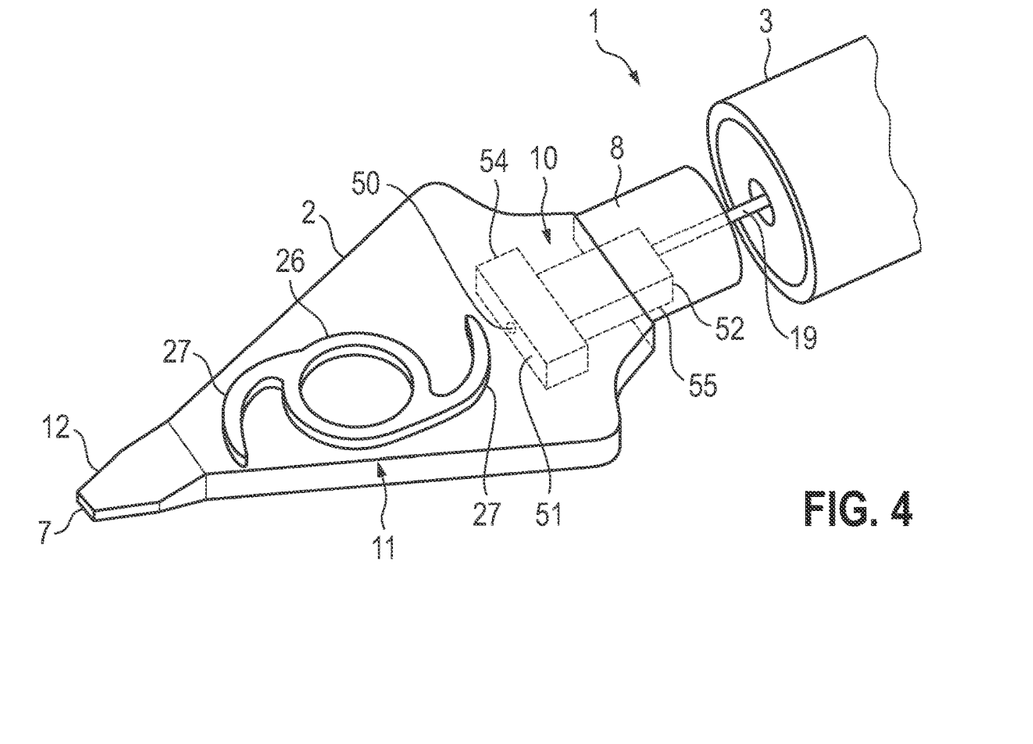
FIG. 4 shows a perspective view of the cartridge with part of the syringe.

As shown in FIGS. 1, 3, and 4, a cartridge 2 has a first opening 7, a second opening 8, a channel 6, which extends from the first opening 7 to the second opening 8 and has a taper 9, an intraocular lens 11 and a cartridge plunger 10. The intraocular lens 11 is arranged in the channel 6 between the first opening 7 and the second opening 8. The cartridge plunger 10 is arranged in the channel 6 between the intraocular lens 11 and the second opening 8 and is set up to first preload the intraocular lens 11 by displacing the cartridge plunger 10 toward the first opening 7, then to fold the intraocular lens 11 by displacing it in the taper 9 and then to push the lens out of the channel 6 via the first opening 7. The channel 6 is closed along its entire circumference or at least partially open on at least one side of the circumference. The cartridge 2 is set up to be coupled to a syringe 3, so that a fluid 30 can be forced into the channel 6 via the second opening 8 with the syringe 3 and the cartridge plunger 10 can thereby be propelled in a direction of insertion 22 toward the first opening 7. The channel 6 is thus set up to allow the fluid 30 to pass from the syringe 3 to the cartridge plunger 10, so that the cartridge plunger 10 can be propelled in the direction of the first opening 7 as the channel 6 is increasingly filled with the fluid 30. The cartridge plunger 10 has a first cartridge-plunger longitudinal end 51, a second cartridge-plunger longitudinal end 52 and a fluid line 50, which extends from the first cartridge-plunger longitudinal end 51 to the second cartridge-plunger longitudinal end 52 and with which the fluid 30 can be forced from the second cartridge-plunger longitudinal end 52 to the first cartridge-plunger longitudinal end 51 and then to the intraocular lens 11, compare FIGS. 1, 3, 5, and 7. The cartridge plunger 10 is thus set up to allow the fluid 30 to pass from the side of the cartridge plunger 10 facing away from the intraocular lens 11 to the side of the cartridge plunger 10 facing the intraocular lens 11. On the side of the cartridge plunger 10 facing the intraocular lens 11, the fluid 30 wets the intraocular lens 11 and thereby reduces its friction.

As can be seen from FIGS. 1, 3 to 5, and 7 to 17, the first cartridge-plunger longitudinal end 51, projected in the direction of insertion 22, can have a larger cross section than the second cartridge-plunger longitudinal end 52, projected in the direction of insertion 22. The beginning and the end of the fluid line 50 belong to the second cartridge-plunger longitudinal end 52 and to the first cartridge-plunger longitudinal end 51. If the first cartridge-plunger longitudinal end 51 has elevations and/or depressions, as shown for example in FIG. 13, then the entire surface of the cartridge plunger 10 facing the intraocular lens 11 belongs to the first cartridge-plunger longitudinal end 51. If the second cartridge-plunger longitudinal end 52 has elevations and/or depressions, as is shown for example in FIGS. 7 to 16, the elevations and depressions belong to the second cartridge-plunger longitudinal end 52.

It is conceivable that the cartridge plunger 10 seals the channel 6 in the region of the first cartridge-plunger longitudinal end 51, such that no fluid 30 can pass the cartridge plunger 10 on its outer circumference. This achieves the effect that the intraocular lens 11, in particular a haptic element 27 of the intraocular lens 11, cannot be clamped between the cartridge plunger 10 and a wall of the channel 6. In addition, the fluid 30 only reaches the intraocular lens 11 via the fluid line 50.

Figure 17:
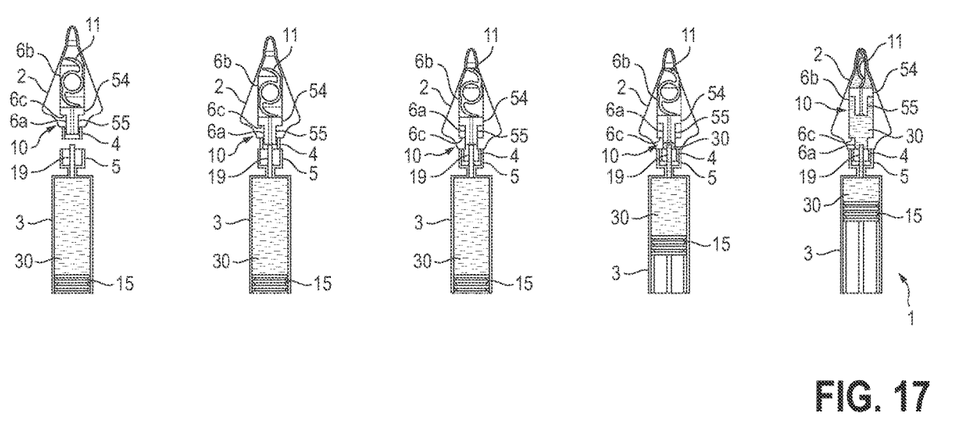
FIG. 17 shows the cartridge and the syringe before and after their assembly to form the injector and the injector in various states of its operation.

FIGS. 1, 3, and 17 show that the channel 6 has a first channel portion 6a, in which the second cartridge-plunger longitudinal end 52 is arranged before the fluid 30 is forced into the channel 6, and which has a first cross section, the normal of which is parallel to the direction of insertion 22 and essentially corresponds to the second cartridge-plunger longitudinal end 52 projected in the direction of insertion 22, and may have a second channel portion 6b, which is arranged between the first channel portion 6a and the first opening 7 and has a second cross section, the normal of which is arranged parallel to the direction of insertion 22 and which is larger than the first cross section, wherein the distance from the first opening 7 to the first channel portion 6a is longer than the extent of the cartridge plunger 10 in the direction of insertion 22. For example, a transition from the first channel portion 6a to the second channel portion 6b may be realized with a step 6c. Alternatively, it is conceivable that the transition is accomplished with a diffuser.

FIGS. 7 to 16 show that the cartridge plunger 10 may have a first portion 54, which has the first cartridge-plunger longitudinal end 51 and is flexible, a second portion 55, which has the second cartridge-plunger longitudinal end 52, and a third portion 56, which is arranged between the first portion 54 and the second portion 55 and has a recess 58a, which is set up to receive parts of the first portion 54 when the cartridge plunger 10 enters the taper 9. In addition, the third portion 56 may have a further recess 58b, which is set up to receive other parts of the first portion 54 when the cartridge plunger 10 enters the taper 9. The cartridge plunger 10 thus has essentially the form of a T before it enters the taper 9 and essentially the form of a pin when the cartridge plunger 10 is displaced up to the first opening 7. The pin may have for example a rectangular, circular, or oval cross section. The cartridge plunger 10, in particular the first portion 54 of the cartridge plunger 10, may include or consist of silicone.

Figure 5:
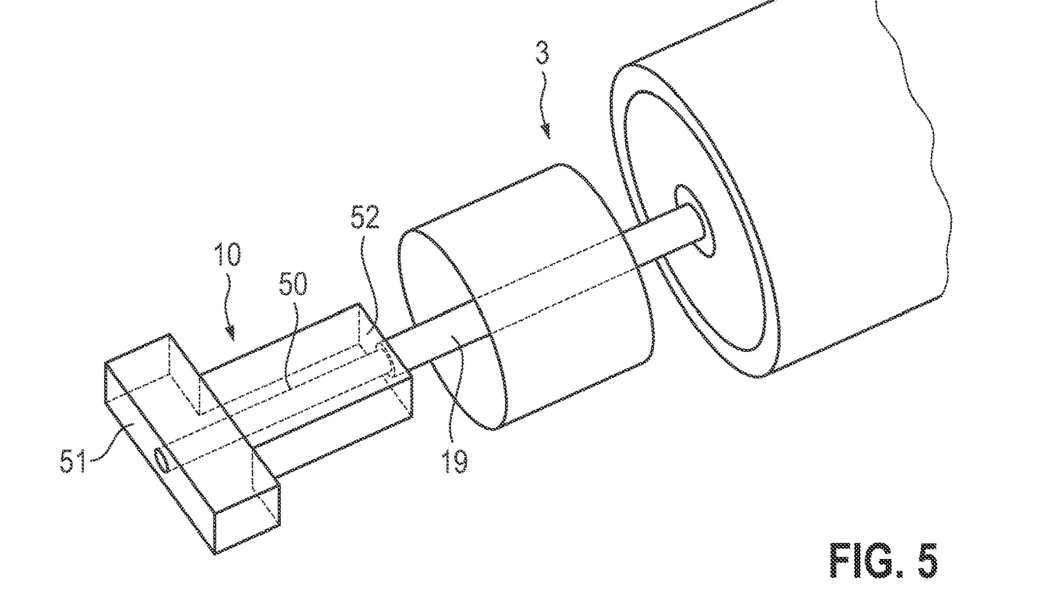
FIG. 5 shows the perspective view according to FIG. 4, but with fewer components.
Figure 6:
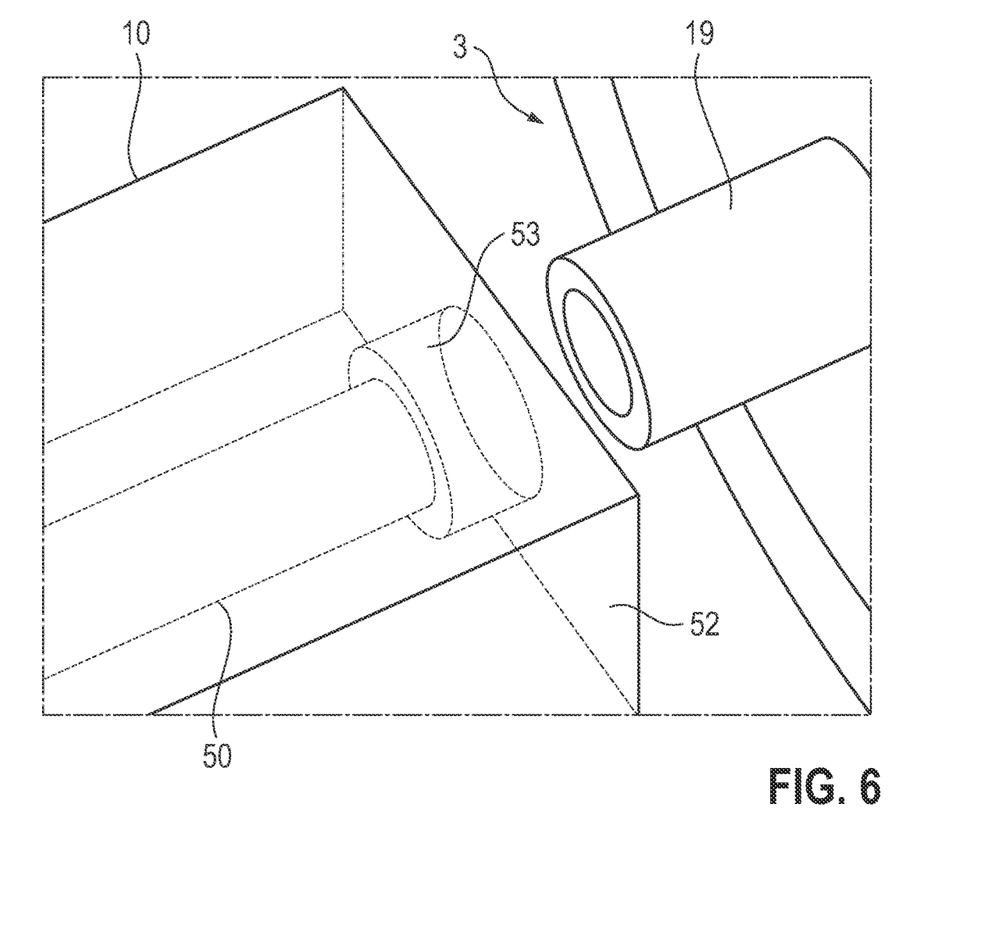
FIG. 6 shows a cannula of the syringe together with part of a cartridge plunger of the cartridge.
Figure 7:
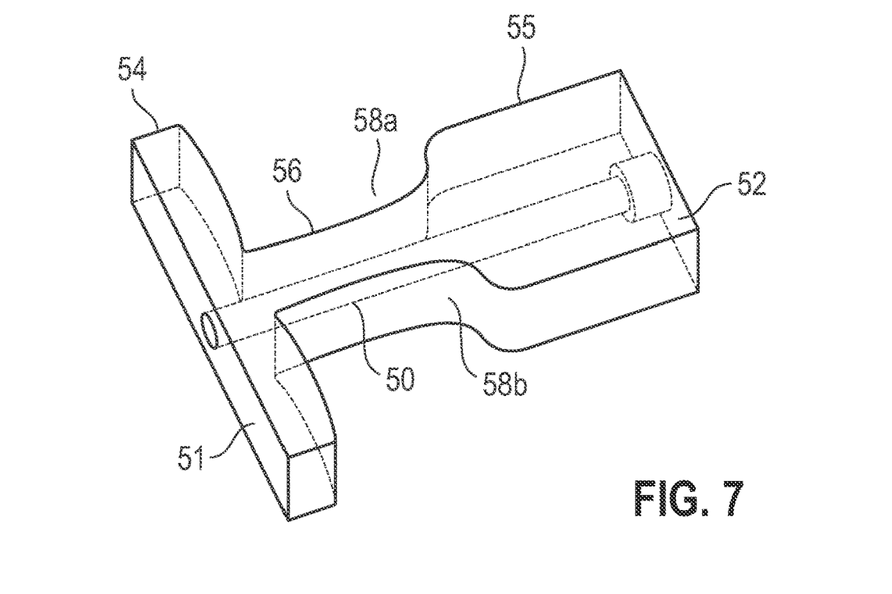
FIGS. 7 to 16 show exemplary embodiments of the cartridge plunger.
Figure 8:
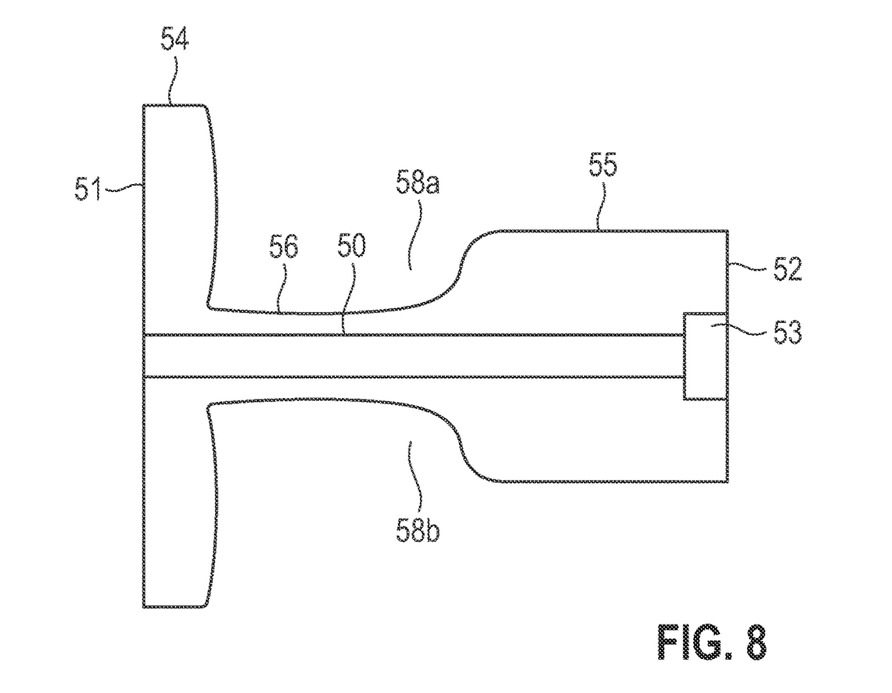
Figure 9:
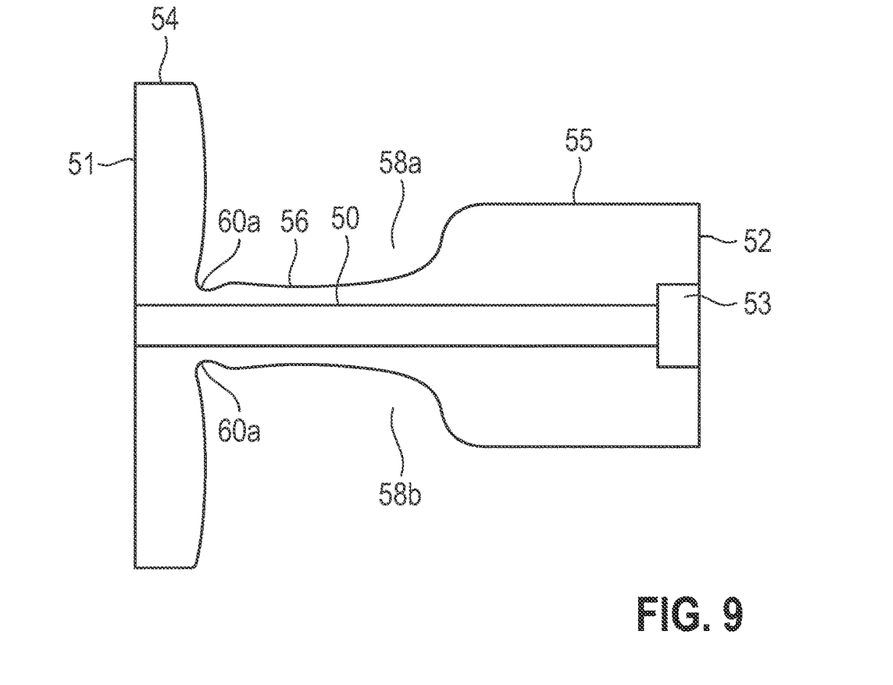

FIGS. 4, 5, and 7 show that, before the cartridge plunger 10 enters the taper, the first cartridge-plunger longitudinal end 51 and the second cartridge-plunger longitudinal end 52 may have a rectangular form. It is also conceivable that, before the cartridge plunger 10 enters the taper, the first cartridge-plunger longitudinal end 51 and the second cartridge-plunger longitudinal end 52 have a circular or oval form.

The first portion 54 may have a groove 60a, 60b, 60d, 60e on its side facing away from the intraocular lens 11, compare FIGS. 9 to 14. The groove 60a may for example be arranged at a radially inner end of the side of the first portion 54 facing away from the intraocular lens 11, compare FIG. 9. It is also conceivable that the cartridge plunger 10 has two of the grooves 60a, which are arranged opposite with respect to the third portion 56.

Figure 10:
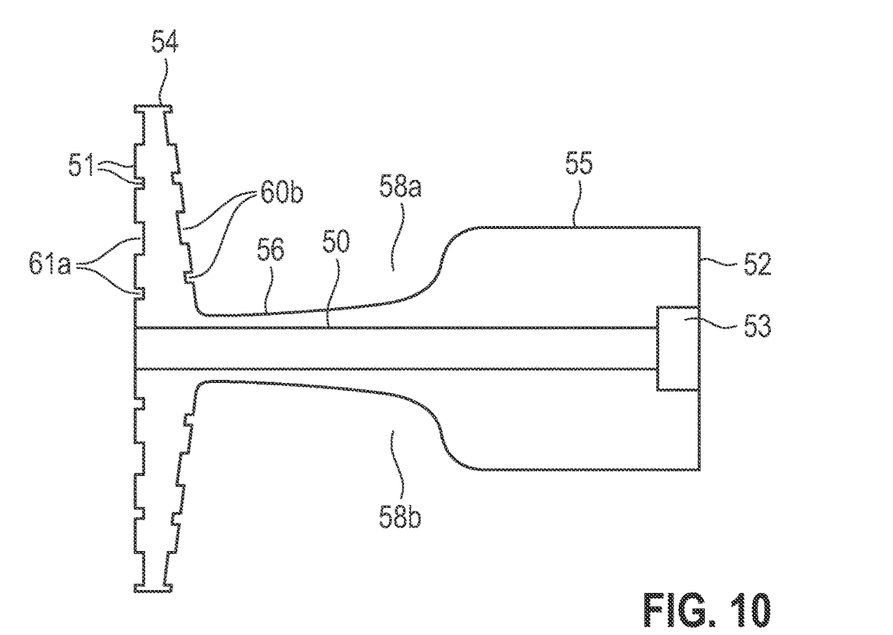
Figure 11:
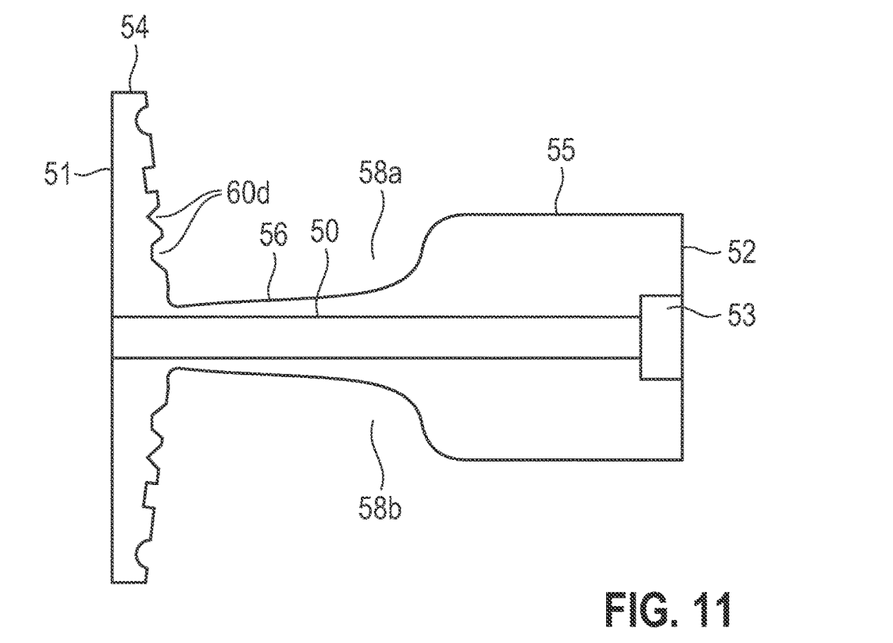
Figure 12:
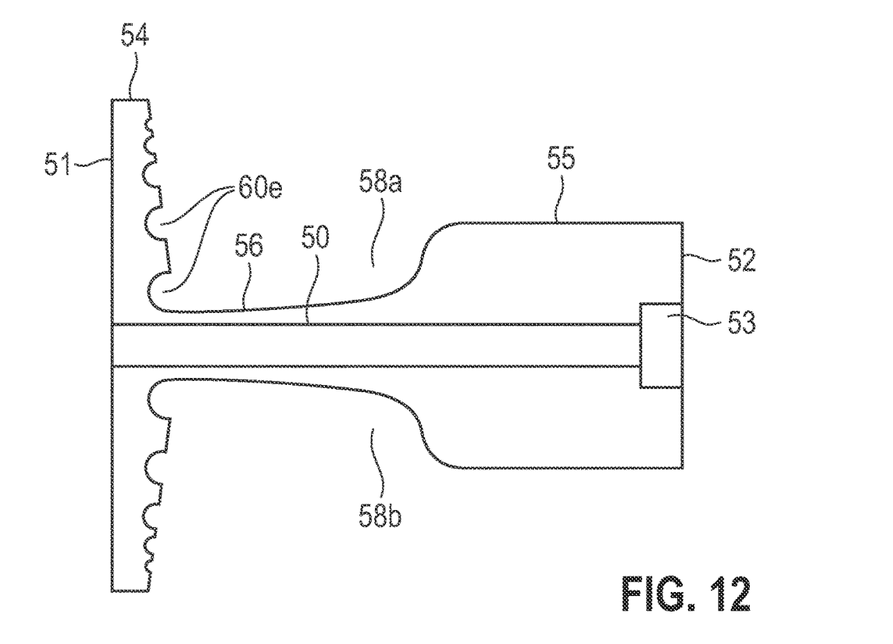

It is also conceivable that several of the grooves 60b, 60d, and 60e are provided, which are arranged at different distances from the third portion 56, compare FIGS. 10 to 12.

FIGS. 10 to 12 also show that the grooves 60*b*, 60*d*, and 60*e* may have a different form. The grooves 60*b*, 60*d* may be at least partially angular in cross section. The grooves 60*d*, 60*e* may be at least partially round in cross section. It is also conceivable that the grooves 60*e* in the cartridge plunger may be configured as alternately round and angular in cross section.

Figure 13:
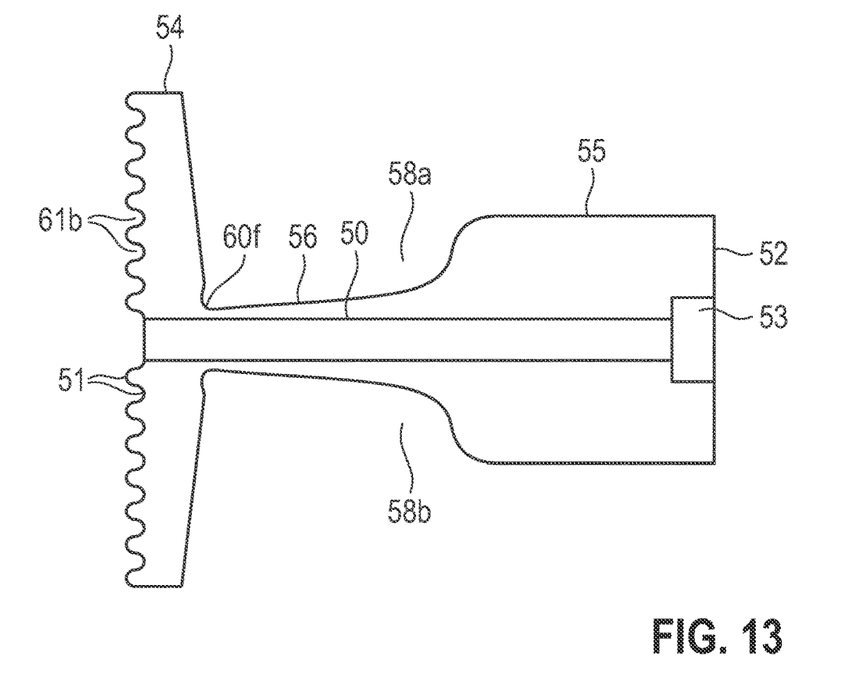
Figure 14:
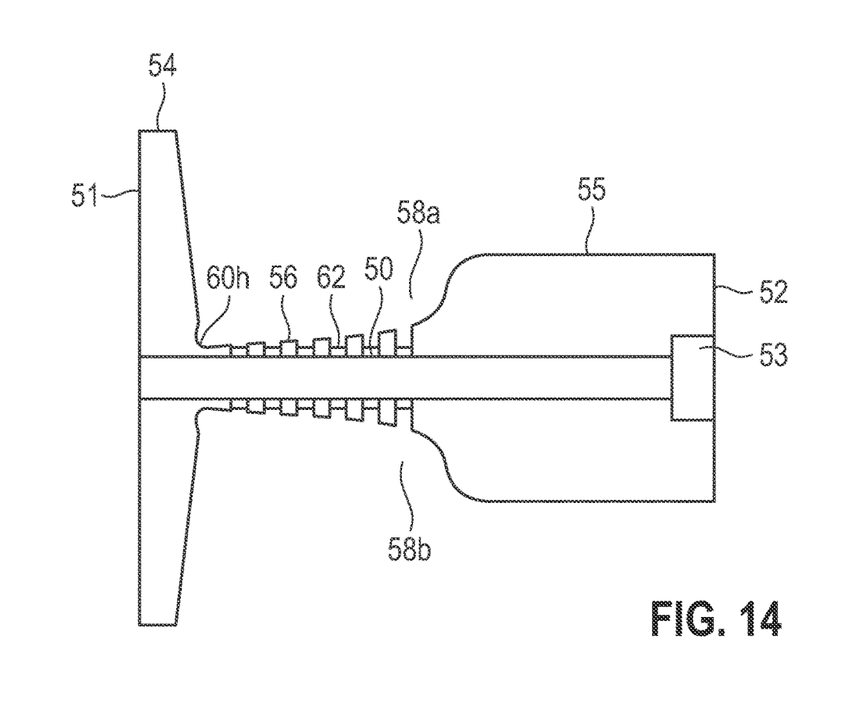
Figure 15:
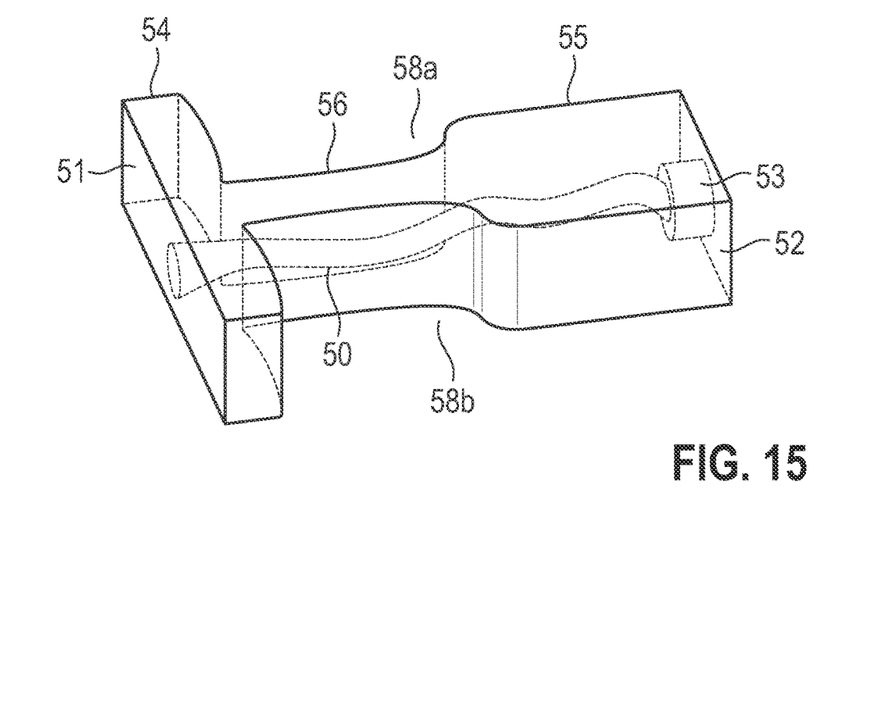
Figure 16:
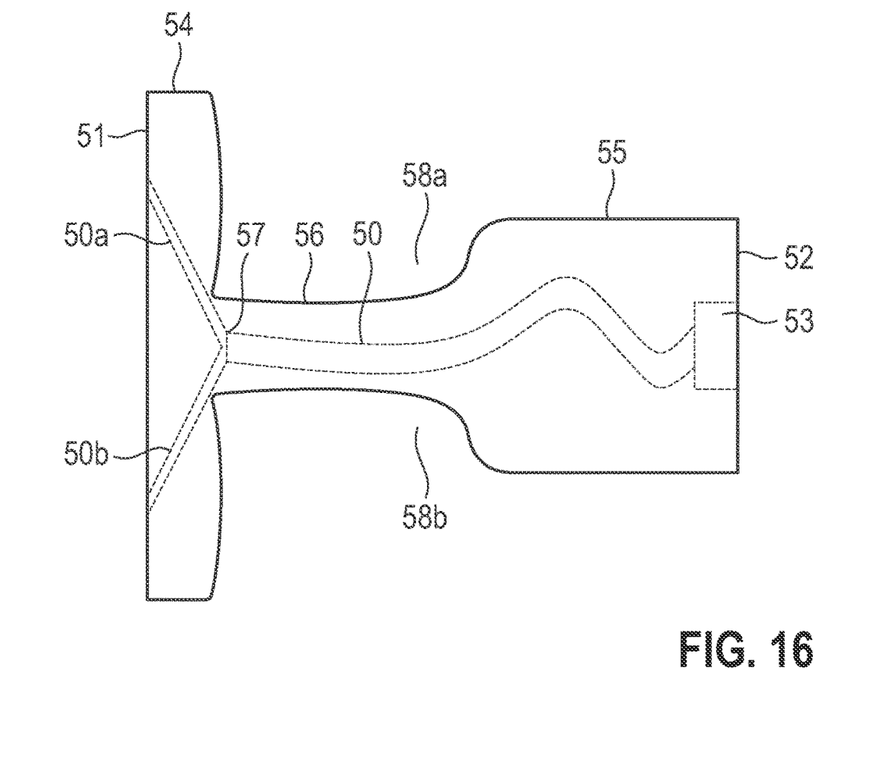

FIGS. 10 and 13 show that the cartridge plunger 10 may have one or more front-side grooves 61 on its side facing the intraocular lens 11. As a result, a contact area of the intraocular lens 11 on the cartridge plunger 10 is reduced, whereby the intraocular lens 11 is less likely to stick to the cartridge plunger 10. The front-side grooves 61*a* may for example be angular in cross section, compare FIG. 10. It is also conceivable that the front-side grooves 61*b* are round in cross section, compare FIG. 13.

The fluid line 50 may also have a fork 57, such that the fluid line 50 has two partial fluid lines 50*a*, 50*b* downstream of the fork 57. As a result, the fluid 30 can exit at two different openings at the first cartridge-plunger longitudinal end 51 and can thus be distributed more evenly in the channel 6 downstream of the cartridge plunger 10. It is also conceivable that the fluid line 50 has several of the forks 57. As a result, the channel 6 has at least three partial fluid lines.

The cartridge 2 may have a first cover, which seals the first opening 7. This can avoid contamination of the intraocular lens 11 while the cartridge 2 is being stored. In the event that the intraocular lens 11 is a hydrophilic intraocular lens to be stored in a storage liquid, escape of the storage liquid from the channel 6 can be avoided by the first cover and the cartridge plunger 10. In addition, the cartridge 2 may have a second cover, which seals the second opening 8. In order to couple the cartridge 2 to the syringe 3, the second cover must first be removed.

FIG. 1 shows that the intraocular lens 11 may have an optical body 26, which is arranged completely between the taper 9 and the cartridge plunger 10. In addition, the intraocular lens 11 may have a haptic element 27, which is attached to the optical body 26. It is conceivable that both the optical body 26 and the haptic element 27 are in a relaxed state.

As can be seen from FIGS. 1 and 3, the cartridge 2 may have a tip 12, in which the first opening 7 is arranged and which is set up to be inserted into the capsular bag of an eye. The tip 12 may be formed as tapering in the direction of the first opening 7. In addition, FIGS. 1 and 3 show that the channel 6 may be straight, which means that the channel 6 has no curve and/or no deflection. According to a further exemplary embodiment, however, the channel 6 may have a deflection.

In addition, FIGS. 1 and 3 show that the cartridge 2 may have a cartridge adapter 4, which is set up to be in engagement with a syringe adapter 5 of the syringe 3 in order to couple the cartridge 2 to the syringe 3. The cartridge adapter 4 may be for example a male adapter of a Luer connection 23, as shown in FIGS. 1 and 3. Alternatively, it is conceivable that the cartridge adapter 4 is a female adapter of a Luer connection 23 or part of a clamping closure, a snap-in closure, a bayonet closure or a screw closure.

FIG. 3 shows an injector 1, which has the cartridge 2 and the syringe 3, wherein the cartridge 2 is coupled to the syringe 3. The syringe 3 contains the fluid 30 and the injector 1 is set up to displace the cartridge plunger 10 in the direction of insertion 22 toward the first opening 7 by forcing the fluid 30 into the channel 6 via the second opening 8 with the syringe 3.

From FIGS. 6 to 16 it can be seen that the cartridge plunger 10 may have at its end facing the syringe 3 a cartridge-plunger recess 53, which is set up to receive the longitudinal end of the cannula 19 facing the cartridge plunger 10 when the cartridge 2 is coupled to the syringe 3. The cartridge-plunger recess 53 may be formed by a widening of the fluid line 50, wherein the widening is arranged in the region of the second cartridge-plunger longitudinal end 52.

Figure 2:
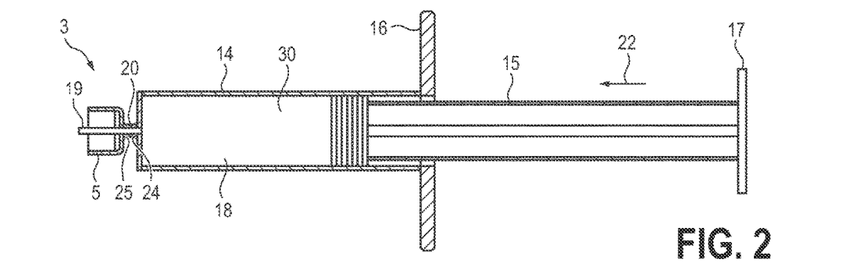
FIG. 2 shows a syringe with a syringe plunger in a first position.

FIGS. 2, 3, and 17 show that the syringe 3 may have a cannula 19, through which the fluid 30 can be forced out of the syringe 3. The cannula 19 may be of such a length that it protrudes into the channel 6. In addition, the cannula 19 may be formed as rigid. The syringe 3 may have a cylinder 14 and a syringe plunger 15, which is mounted in the cylinder 4 in a longitudinally displaceable manner, wherein the cylinder 14 and the syringe plunger 15 delimit a cylinder interior 18, in which the fluid 30 is arranged and which is connected to the cannula 19 in a fluid-conducting manner.

In FIG. 17, the injector 1 is shown at five different points in time before and after its assembly and in its operation, the time progressing from left to right. At the first point in time, the cartridge 2 and the syringe 3 are separated from one another. At the second point in time, the beginning of a coupling of the cartridge 2 to the syringe 3 is shown, with the cartridge adapter 4 and the syringe adapter 5 touching. At the third point in time, the cartridge 2 and the syringe are even closer together and completely coupled to one another. This can be performed for example by screwing the cartridge adapter 4 to the syringe adapter 5. The cannula 19 can be of such a length that, when the cartridge 2 is coupled to the syringe 3, as shown at the third point in time, the cannula 19 displaces the cartridge plunger 10 so far in the direction of the first opening 7 that the intraocular lens 11 is preloaded. It is conceivable that the intraocular lens 11 is also folded thereby. By preloading and optionally folding the intraocular lens 11, a force of resistance R1 is generated between the haptic element 27 of the intraocular lens 11 and the wall of the channel 6 in the region of the taper 9 and sealing of the channel 6 is brought about by the intraocular lens 11. If the syringe plunger 15 in the injector 1 is displaced from a first position, cf. FIG. 2 and the third point in time in FIG. 17, along the direction of insertion 22 to a second position, cf. FIG. 3 and the fourth point in time in FIG. 17, the cylinder interior 18 is reduced and the fluid 30 is forced from the cylinder interior 18 into the cannula 19. The fluid 30 then flows out of the cannula 19 and enters the channel 6 in a region between the cartridge plunger 10 and the second opening 8. From there, the fluid 30 reaches the intraocular lens 11 via the fluid line 50. The friction of the fluid 30 in the fluid line 50 generates a force of resistance R2.

Depending on the force of resistance R2, by fluid friction in the fluid line 50 and a force of resistance R3 in the form of friction between the cartridge plunger 10 and the wall of the channel 6, there is an acceleration of the cartridge plunger 10. During this phase, the force of resistance R1 is larger than the force F effectively acting on the cartridge plunger 10 due to the fluid pressure. R1>>F. The acting force is initially only sufficient to preload the intraocular lens 11. At the same time, the cartridge plunger 10 is displaced in the direction of the first opening 7 due to a force F exerted by the fluid 30 on the second cartridge-plunger longitudinal end 52. Due to the friction of the cartridge plunger 10 on the wall of the channel 6, the force of resistance R3 is generated. In this phase (R2>R3)<R1. By suction and the resulting displacement of the cartridge plunger 10 as a result of the fluid friction R2, the contact surface area of the fluid 30 on the side of the second cartridge-plunger longitudinal end 52 increases. By further pressing of the syringe plunger 15, the fluid pressure in the channel 6 additionally increases, resulting in an additional increase in the force acting on the cartridge plunger 10, such that the cartridge plunger 10 is displaced in the direction of the first opening and the intraocular lens 11 is folded thereby.

At the fourth point in time, the second cartridge-plunger longitudinal end 52 is arranged in the first channel portion 6a and the fluid 30 also acts on the second cartridge-plunger longitudinal end 52. At the fifth point in time, the second cartridge-plunger longitudinal end 52 is arranged in the second channel portion 6b and the fluid 30 additionally acts on the side of the first portion 54 facing away from the intraocular lens 11. Assuming that the pressure of the fluid 30 is the same at the fourth point in time and the fifth point in time, the force F is stronger at the fifth point in time than at the fourth point in time, so that: F>R1. It is consequently then possible to push the intraocular lens 11 out of the first opening 7.

As can be seen from FIG. 3, the cartridge 2 may have a cartridge adapter 4 and the syringe 3 may have a syringe adapter 5, through which the cannula 19 extends, wherein the cartridge adapter 4 and the syringe adapter 5 are in engagement with one another, whereby the cartridge 2 is coupled to the syringe 3 and the injector 1 is sealed in the region of the cartridge adapter 4 and the syringe adapter 5. In order to bring the cartridge adapter 4 into engagement with the syringe adapter 5, this can be performed with a movement of the cartridge 2 relative to the syringe 3 in a direction opposite to the direction of flow that the fluid 30 in the cannula 19 assumes when it is forced out of the syringe 3, or against the direction of insertion 22. The cartridge adapter 4 and the syringe adapter 5 may be set up to be in positive engagement with one another when the cartridge 2 is coupled to the syringe 3. FIG. 3 shows that the cartridge adapter 4 and the syringe adapter 5 may form a Luer connection 23. In the case of the Luer connection 23, the injector 1 is sealed at those surfaces of the cartridge adapter 4 and the syringe adapter 5 where the cartridge adapter 4 and the syringe adapter 5 touch. With the Luer connection 23 it is conceivable that the cartridge adapter 4 is the male adapter and the syringe adapter 5 is the female adapter, as is also shown in FIG. 3. Alternatively, it is conceivable that the cartridge adapter 4 is the female adapter and the syringe adapter 5 is the male adapter. As an alternative to the Luer connection 23, the cartridge adapter 4 and the syringe adapter 5 may form a clamping closure, a snap-in closure, a bayonet closure or a screw closure.

The injector 1 may have an adapter interior 21, which is directly adjacent to the second opening 8 and is delimited by the cartridge adapter 4. In addition, the syringe 3 may have a tube 20, which has a first longitudinal end 24 and a second longitudinal end 25. The first longitudinal end 24 is attached to the cylinder 14 and the syringe adapter 5 is attached to the second longitudinal end 25. It is conceivable that the cannula 19 extends through the tube 21. As a result, the cannula 19 can be attached particularly firmly to the cylinder 14.

FIGS. 1 and 3 show that the cartridge 2 may have a cartridge wing 13, which protrudes outward from the remaining cartridge 2. As a result, the cartridge 2 can be gripped easily and thus easily coupled to the syringe 3 by hand. FIGS. 2 and 3 show that the cylinder 14 may have at its end facing away from the cannula 19 a handle 16, which protrudes outward from the remaining cylinder 14. In addition, the syringe plunger 15 may have at its end facing away from the cannula 19 a thickening 17, which protrudes outward from the remaining syringe plunger 15.

The fluid may include a lubricant and/or a physiological saline solution or consist of the lubricant and/or the physiological saline solution. The lubricant may be an ophthalmic viscoelastic device (OVD). The ophthalmic viscoelastic device has a comparatively high viscosity and is therefore particularly suitable for propelling the cartridge plunger 10.

It is understood that the foregoing description is that of the exemplary embodiments of the disclosure and that various changes and modifications may be made thereto without departing from the spirit and scope of the disclosure as defined in the appended claims.

LIST OF REFERENCE NUMERALS

1 Injector
2 Cartridge
3 Syringe
4 Cartridge adapter
5 Syringe adapter
6 Channel
6a First channel portion
6b Second channel portion
6c Step
7 First opening
8 Second opening
9 Taper
10 Cartridge plunger
11 Intraocular lens
12 Tip
13 Cartridge wing
14 Cylinder
15 Syringe plunger
16 Handle
17 Thickening
18 Cylinder interior
19 Cannula
20 Tube
21 Adapter interior
22 Direction of insertion
23 Luer connection
24 First longitudinal end
25 Second longitudinal end
26 Optical body
27 Haptic element
30 Fluid
50 Fluid line
50a Partial fluid line
50b Partial fluid line
51 First cartridge-plunger longitudinal end
52 Second cartridge-plunger longitudinal end
53 Cartridge-plunger recess
54 First portion
55 Second portion
56 Third portion
57 Fork
58a Recess
58b Further recess
60a, 60b, 60d, 60e Groove
61 Front-side groove
62 Transverse-side groove

What is claimed is:

1. A cartridge, comprising:
a first opening;
a second opening;

a channel, which extends from the first opening to the second opening and which has a taper;

an intraocular lens arranged in the channel between the first opening and the second opening; and a cartridge plunger arranged in the channel between the intraocular lens and the second opening and set up to first preload the intraocular lens by displacing the cartridge plunger toward the first opening, then to fold the intraocular lens by displacing the intraocular lens in the taper, and then to push the intraocular lens out of the channel via the first opening, wherein the cartridge is set up to be coupled with a syringe, such that a fluid can be forced into the channel via the second opening with the syringe and the cartridge plunger can thereby be propelled in a direction of insertion toward the first opening, wherein the cartridge plunger has a first cartridge-plunger longitudinal end, a second cartridge-plunger longitudinal end, and a fluid line, which extends from the first cartridge-plunger longitudinal end to the second cartridge-plunger longitudinal end, and via which the fluid can be forced in from the second cartridge-plunger longitudinal end to the first cartridge-plunger longitudinal end and then to the intraocular lens, wherein the cartridge plunger seals the channel in an area of the first cartridge-plunger longitudinal end, such that no fluid can pass through the cartridge plunger on its outer circumference, and wherein the cartridge plunger has a first portion, which has the first cartridge-plunger longitudinal end and which is flexible, a second portion, which has the second cartridge-plunger longitudinal end, and a third portion, which is arranged between the first portion and the second portion and which has a recess, which is set up to receive parts of the first portion when the cartridge plunger enters the taper.

2. The cartridge as claimed in claim 1, wherein the first cartridge-plunger longitudinal end, projected in the direction of insertion, has a larger cross section than the second cartridge-plunger longitudinal end, projected in the direction of insertion.

3. The cartridge as claimed in claim 2, wherein the channel has a first channel portion, in which the second cartridge-plunger longitudinal end is arranged before the fluid is forced into the channel and which has a first cross section, a normal of which is arranged parallel to the direction of insertion and which substantively corresponds to the second cartridge-plunger longitudinal end projected in the direction of insertion, and a second channel portion arranged between the first channel portion and the first opening and which has a second cross section, a normal of which is arranged parallel to the direction of insertion and which is larger than the first cross section, and wherein a distance from the first opening to the first channel portion is longer than an extent of the cartridge plunger in the direction of insertion.

4. The cartridge as claimed in claim 1, wherein the first portion has a groove on a side of the first portion facing away from the intraocular lens.

5. The cartridge as claimed in claim 1, wherein the fluid line has a curve.

6. An injector, comprising:
the cartridge as claimed in claim 1; and
the syringe,
wherein the cartridge is coupled to the syringe,
wherein the syringe contains the fluid, and
wherein and the injector is set up to displace the cartridge plunger in the direction of insertion toward the first opening by forcing the fluid into the channel via the second opening with the syringe.

7. The injector as claimed in claim 6, wherein the syringe has a cannula through which the fluid can be forced out of the syringe.

8. The injector as claimed in claim 7, wherein the cannula is of such a length that, when the cartridge is coupled to the syringe, the cannula displaces the cartridge plunger so far in a direction of the first opening that the intraocular lens is thereby preloaded.

9. The injector as claimed in claim 7, wherein the cartridge plunger has at an end facing the syringe a cartridge-plunger recess set up to receive a longitudinal end of the cannula facing the cartridge plunger when the cartridge is coupled to the syringe.

* * * * *